United States Patent [19]

Arnold, Jr.

[11] 4,051,202

[45] Sept. 27, 1977

[54] METHOD FOR SEPARATING MONO- AND DI-OCTYLPHENYL PHOSPHORIC ACID ESTERS

[75] Inventor: Wesley D. Arnold, Jr., Oak Ridge, Tenn.

[73] Assignee: The United States of America as represented by the United States Energy Research and Development Administration, Washington, D.C.

[21] Appl. No.: 632,749

[22] Filed: Nov. 17, 1975

[51] Int. Cl.$^2$ .............................................. C07F 9/09
[52] U.S. Cl. .................................................. 260/990
[58] Field of Search ........................................ 260/990

[56] References Cited

U.S. PATENT DOCUMENTS 2,658,909  11/1953  Crandall et al. ..................... 260/990

FOREIGN PATENT DOCUMENTS 41-4977  3/1966  Japan ..................................... 260/990
746,535  3/1956  United Kingdom ................. 260/990

Primary Examiner—Anton H. Sutto
Attorney, Agent, or Firm—Dean E. Carlson; Stephen D. Hamel; Allen H. Uzzell

[57] ABSTRACT

A method for separating mono-octylphenyl phosphoric acid ester and di-octylphenyl phosphoric acid ester from a mixture thereof comprises reacting the ester mixture with a source of lithium or sodium ions to form a mixture of the phosphate salts; contacting the salt mixture with an organic solvent which causes the dioctylphenyl phosphate salt to be dissolved in the organic solvent phase and the mono-octylphenyl phosphate salt to exist in a solid phase; separating the phases; recovering the phosphate salts from their respective phases; and acidifying the recovered salts to form the original phosphoric acid esters.

4 Claims, No Drawings

METHOD FOR SEPARATING MONO- AND DI-OCTYLPHENYL PHOSPHORIC ACID ESTERS

BACKGROUND OF THE INVENTION

This invention was made in the course of, or under, a contract with the Energy Research and Development Administration. This invention relates to the art of separating mono-octylphenyl and di-octylphenyl esters of phosphoric acid and more particularly to a solid/liquid separation process where the mono-octylphenyl phosphoric acid ester is separated and recovered from the solid phase.

The separation process of this invention is particularly useful for providing a substantially pure mono-octylphenyl phosphoric acid ester for use as a make-up component for the extractant in a process for recovering uranium from wet-process phosphoric acid. Such a process is more fully described in commonly assigned U.S. Pat. No. 3,835,214 issued Sept. 10, 1974 to Hurst et al. for "Oxidative Stripping Process for the Recovery of Uranium from Wet-Process Phosphoric Acid" the disclosure of which is incorporated herein in its entirety by reference.

In the Hurst et al. process, uranium values present in the feed solution (5 to 6 M $H_3PO_4$) are concentrated in a first cycle by a factor of 70 to 100 by extracting into an organic phase (typically a mixture of mono- and di-octylphenyl esters of orthophosphoric acid dissolved in an inert diluent) and stripping from the organic phase into an 8 to 12 M $H_3PO_4$ solution containing an oxidizing agent. During the course of operation of the Hurst et al. process, the first cycle extractant which is continuously recycled becomes depleted in the mono-octylphenyl ester due to its slight solubility in the aqueous $H_3PO_4$ solution.

It has been found that the efficiency of the first cycle extraction is somewhat dependent upon the ratio of mono- to diester in the extractant. The commercially available octylphenyl phosphoric acid ester is approximately a 1 to 1 molar ratio of the mono- and di-esters. Satisfactory extraction efficiency is attainable with a molar ratio of mono- to di-ester in the range of from about 1-1 to about 1-7. If the first cycle extractant becomes more depleted in the mono-ester, the extractive efficiency diminishes rapidly. In order to maintain the preferred mono- to di-ester ratio, either the first cycle extractant must be periodically renewed or a separated mono-ester must be periodically added to the recycled extractants as a make-up component.

PRIOR ART

In the prior art, mono- and di-octylphenyl phosphoric acid esters have been separated by various solvent extraction processes which involved the formation of sodium salts of the ester and solent extraction based upon the preferential distribution of the di-substituted salt to organic solvents and the mono-substituted salt to aqueous solvents or ethylene gylcol. Typical examples of such solvent extraction processes are reported by D. R. Peppard et al. in Journal of Inorganic Nuclear Chemistry, Vol. 7, p. 231 (1958), and Steward et al. in Journal of the American Chemical Society, Vol. 73, p. 1377 (1951). These prior art processes require successive extraction stages and large amounts of solvents and would be more cumbersome to carry out on an industrial scale than the process of this invention.

SUMMARY OF THE INVENTION

It is an object of this invention to provide a simple, efficient solid/liquid separation process for mono- and di-octylphenyl phosphoric acid esters. This and other objects are accomplished by providing a method of separating a mono-octylphenyl phosphoric acid ester from a mixture containing mono- and di-octylphenyl phosphoric acid esters, said method comprising contacting said mixture with an organic solvent capable of selectively dissolving alkali metal di-octylphenyl phosphate salt from a mixture of alkali metal mono- and di-octylphenyl phosphate salts while leaving alkali metal mono-octylphenyl phosphate salt in a solid phase, said alkali metal being selected from the group of sodium and lithium; contacting said mixture with a source of ions of said alkali metal to cause alkali metal mono-octylphenyl phosphate salt to be distributed in a solid phase; separating the resulting alkali metal mono-octylphenyl phosphate salt in said solid phase from said organic solvent and acidifying the separated mono-octylphenyl phosphate salt to form the mono-octylphenyl phosphoric acid ester. If desired, the dioctylphenyl phosphoric acid ester may be recovered from the organic solvent phase and purified.

DETAILED DESCRIPTION

One inventive aspect of this invention is the discovery that the sodium or lithium salts of mono- and di-octylphenyl phosphoric acid esters are separable from a mixture thereof with a relatively high degree of efficiency in certain organic solvents by the selective precipitation of the sodium or lithium mono-octylphenyl phosphate salts. This in unexpected since the corresponding potassium salts have been observed not to exhibit similar behavior and the alkali metal salts of other mono-alkyl substituted phosphoric acid esters are soluble in aliphatic alcohols. The general term mono- or di-octylphenyl phosphoric acid as used herein (which is more accurately a mono- or di-substituted acid ester) refers to the mono- and di-substituted octylphenyl esters of orthophosphoric acid, having the general formula $(RO)_x—PO—(OH)_y$ where R represents a phenyl group having an octyl group in the para position (either n-octyl or a branched octyl isomer) and where $x = 1, y = 2$ for the mono-substituted ester and $x = 2, y = 1$ for the di-substituted ester. The alkali metal phosphate salts result when the hydrogen in the (OH) groups (which are ionizable hydrogen) are replaced by alkali metal ions. The octylphenyl isomers ordinarily used in the Hurst et al. process are the mono- and dipara 1,1,3,3, tetramethylbutylphenyl orthophosphoric acid esters. Within the scope of this invention are other octylphenyl isomers which have utility as extractants for uranium and other metals and which are separable in a like manner.

In order for the separation process of this invention to be efficiently operable, it is required that the mono- and disubstituted ester mixture be reacted with a source of ions of an alkali metal consisting of sodium or lithium to form a mixture of sodium or lithium mono-octylphenyl and di-octylphenyl phosphate salt, which as shown herein are separable from one another by the selective precipitation of the mono-substituted salt. The salt mixture can be easily formed by contacting the aforementioned ester mixture with NaOH, LiOH, $Na_2CO_3$ or $Li_2CO_3$ to both neutralize the acid and form the sodium or lithium salts, however other Na or Li reagents which provide sodium or lithium ions which would react with the esters to form the phosphate salts would also be operable in the subject process. Either concurrently with or after the formation of the phosphate salts, it is necessary that the salt mixture be contacted with an organic solvent in which the di-octylphenyl phosphate salt is selectively soluble and in which the mono-octylphenyl phosphate salt has very low solubility, so that the organic solvent will contain the major portion of the di-octylphenyl phosphate salt in solution while leaving the major portion of the mono-octylphenyl phosphate salt in a solid phase. Of course, the lower the solubility of the mono-octylphenyl phosphate salt, the greater the recovery and the more efficient the separation.

Satisfactory separation has been achieved with aliphatic alcohols, preferably absolute alcohols, as the organic solvent, e.g., methanol, ethanol, n-propanol and isopropanol. Within the scope of this invention are other aliphatic alcohols such as n-butanol, 2-butanol, tert-butanol, et seq. and other organic solvents capable of selectively dissolving sodium or lithium di-octylphenyl phosphate salt from a mixture of sodium or lithium mono- or di-octylphenyl phosphate salt while leaving a major portion of mono-octylphenyl phosphate salt in a solid phase. With the benefit of this disclosure such organic solvents can be regarded as equivalents in the process of this invention.

In the subject process, after the distribution of the salts into the solvent and solid phase, the individual salts may be acidified and recovered from their respective phase by any suitable process. For example, the phases may be first separated by any solid/liquid separation process, e.g., filtration, centrifugation, etc. After the phases are separated, the solid phase containing the mono-substituted phosphate salt may be dissolved in a suitable solvent (e.g., water) acidified (e.g., with a mineral acid like HCl) and the resulting mono-octylphenyl phosphoric acid recovered by solvent extraction with an organic solvent, for example diethyl ether, and evaporated to dryness. If desired, di-octylphenyl phosphoric acid may be easily recovered from the solvent phase by evaporating the solvent and reacting the residue with a mineral acid to acidify the salt to di-octylphenyl phosphoric acid which may be extracted into a water-immiscible organic solvent such as dibutyl ether, or benzene and evaporated to dryness.

DESCRIPTION OF THE PREFERRED EMBODIMENT

In order to demonstrate the operability of the subject separation process, the following example is presented. The example is a separation of laboratory scale but may be readily amplified to industrial scale. It should be understood that the subject process is a solid/liquid phase separation dependent upon the difference in solubilities of mono- and di-octylphenyl phosphate salts in certain organic solvents. The preferred solvents are the aliphatic alcohols having 1–3 carbon atoms per molecule, because of their ready availability and the efficiency of the separation. The operability of the subject process for separating the esters depends not upon the specific reagents employed but upon the function performed; that is, formation and selective distribution of the major portion of sodium or lithium mono-octylphenyl phosphate salt in a solid phase in an organic solvent medium, recovering the mono- and di-substituted salts from their respective phases, and acidifying the salts to form the initial acids. The preferred method for carrying out the subject separation process is first dissolving the acid ester mixture in the organic solvent and then reacting the resulting acid solution with a compound such as LiOH, NaOH, $Li_2CO_3$, or $Na_2CO_3$ to both neutralize the acid and form the alkali metal salts which selectively distribute between the solvent and a solid phase.

EXAMPLE I

Commercial grade octylphenyl phosphoric acid was obtained from Mobil Chemical Company; P.O. Box 26683; Richmond, Va. and identified as octylphenyl acid phosphate containing a mixture of mono-para-1,1,3,3, tetramethylbutylphenyl orthophosphoric acid represented by the formula

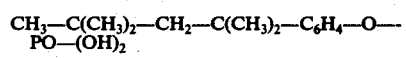

and di-para 1,1,3,3 tetramethylbutylphenyl orthophosphoric acid, represented by the formula

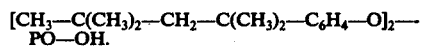

The mixture was analyzed and found to contain 43.8% by weight mono-substituted acid and 53.7% by weight di-substituted acid. Fifty grams of the commercial mixture was dissolved in 500 ml. of absolute ethyl alcohol at room temperature. Twenty-five ml. of 10 M NaOH was slowly added and a bulky white precipitate was formed. Most of the precipitate appeared after the acid mixture had been neutralized, however, a limited recovery of solids is possible before the end point is reached. The major amount of the solid phase was observed to precipitate within a pH range of about 10 to 11.5. The preferred pH range may vary somewhat depending upon the solvent used. It is, of course, within the skill of the art to determine the optimum pH for the precipitation in a particular solvent. The solids were filtered from the solution and washed with about 97 vol. % ethyl alcohol (remainder water). The solid phase is slightly soluble in absolute ethanol but shows virtually no solubility in 97% ethanol. The solids were reslurried in 500 ml. of the 97% ethyl alcohol, again filtered, and the filtrate washed with 97% ethyl alcohol. The solids were then dissolved in about 400 ml. of water to form a slightly yellow solution. Addition of 20 ml. of 6 M HCl (acidification) produced a gummy white precipitate. The precipitate was dissolved by contacting the suspension with three successive portions (200 ml. each) of diethyl ether. The resulting ether solution was scrubbed with 100 ml. of 1 M HCl and filtered. The ether was evaporated to dryness in a vacuum dessicator to yield 16.4 g. of white solids residue. The final product was assayed at 98.5% mono-octylphenyl-orthophosphoric acid. The product yield was approximately 74%.

While the bulk of this disclosure is directed to providing a source of the mono-substituted ester, the di-octylphenyl phosphoric acid ester, which is independently useful as a metal extractant as in the Hurst et al. process, may also be recovered from the organic solvent phase if desired. This may be easily accomplished by removing the organic solvent by evaporation and reacting with a mineral acid to acidify the salt to di-octylphenyl phosphoric acid, which may be extracted into a water-immiscible organic solvent such as benzene and evaporated to dryness.

While the foregoing example demonstrates sequential solvent extractions and washings to achieve very high purity, such purity is not essential to provide a make-up component for use in the Hurst et al. process, since the first cycle extractant is a mixture having a relatively broad operable range of proportions.

What is claimed is:

1. A method of separating a mono-octylphenyl phosphoric acid ester from a mixture containing mono- and di-octylphenyl phosphoric acid esters, said method comprising:
   a. contacting said mixture with an organic solvent selected from the group consisting of methanol, ethanol, n-propanol, isopropanol, n-butanol, 2-butanol, and tert-butanol;
   b. contacting said mixture with a source of ions of an alkali metal selected from the group consisting of sodium and lithium to cause alkali metal mono-octylphenyl phosphate salt to be distributed in a solid phase;
   c. separating the resulting alkali metal mono-octylphenyl phosphate salt in said solid phase from said organic solvent; and
   d. acidifying the separated mono-octylphenyl phosphate salt to form the mono-octylphenyl phosphoric acid ester.

2. The method of claim 1 further comprising the steps separating alkali metal di-octylphenyl phosphate salt from the organic solvent subsequent to step C and acidifying the separated di-octylphenyl phosphate salt to form the di-octylphenyl phosphoric acid ester.

3. The method of claim 1 wherein said source of ions of said alkali metal is selected from the group consisting of NaOH, LiOH, $Na_2CO_3$ and $Li_2CO_3$.

4. The method of claim 3 wherein steps $a$ and $b$ are carried out by first dissolving said ester mixture in said organic solvent and reacting the resulting acid solution with said source of ions of said alkali metal to cause selective precipitation of alkali metal mono-octylphenyl phosphate salt.

* * * * *